(12) United States Patent
Liberman Paz et al.

(10) Patent No.: US 12,257,110 B1
(45) Date of Patent: *Mar. 25, 2025

(54) SYSTEM AND METHOD FOR CONSTRUCTING A THREE-DIMENSIONAL MODEL OF TEETH AND ADJOINING TISSUES IN AN ORAL CAVITY OF AT LEAST ONE USER

(71) Applicants: Gerard Andre Philip Liberman Paz, San Diego, CA (US); Javier Ignacio Liberman Salazar, Santiago (CL); Felipe Ignacio Pesce Bentjerodt, Santiago (CL); Carlos Julio Santander Guerra, Santiago (CL); Cristobal Gaspar Ignacio Pizarro Venegas, Santiago (CL); Diego Facundo Lazcano Arcos, Santiago (CL); Andres Garabed Baloian Gacitua, Santiago (CL); David Caro Benado, Santiago (CL)

(72) Inventors: Gerard Andre Philip Liberman Paz, San Diego, CA (US); Javier Ignacio Liberman Salazar, Santiago (CL); Felipe Ignacio Pesce Bentjerodt, Santiago (CL); Carlos Julio Santander Guerra, Santiago (CL); Cristobal Gaspar Ignacio Pizarro Venegas, Santiago (CL); Diego Facundo Lazcano Arcos, Santiago (CL); Andres Garabed Baloian Gacitua, Santiago (CL); David Caro Benado, Santiago (CL)

( * ) Notice: Subject to any disclaimer, the term of this patent is extended or adjusted under 35 U.S.C. 154(b) by 0 days.

This patent is subject to a terminal disclaimer.

(21) Appl. No.: 18/919,689

(22) Filed: Oct. 18, 2024

Related U.S. Application Data
(63) Continuation-in-part of application No. 18/127,945, filed on Mar. 29, 2023, now Pat. No. 12,154,222.

(51) Int. Cl.
*A61C 13/34* (2006.01)
*A61B 1/00* (2006.01)
(Continued)

(52) U.S. Cl.
CPC .......... *A61C 13/34* (2013.01); *A61B 1/00016* (2013.01); *A61B 1/24* (2013.01);
(Continued)

(58) Field of Classification Search
CPC ............... A61C 13/34; G06T 7/593; G06T 2207/10028; G06T 2207/30036; A61B 1/00016; A61B 1/24
(Continued)

(56) References Cited

U.S. PATENT DOCUMENTS

| | | | |
|---|---|---|---|
| 2014/0146142 A1* | 5/2014 | Duret ..................... | A61C 19/04 348/46 |
| 2020/0107915 A1* | 4/2020 | Roschin ................. | A61C 13/34 |
| 2023/0102949 A1* | 3/2023 | Boyle .................... | H04N 13/122 345/423 |

* cited by examiner

*Primary Examiner* — Hai Tao Sun
(74) *Attorney, Agent, or Firm* — Boris Leschinsky

(57) ABSTRACT

A system to build a three-dimensional model of a user's teeth and adjoining tissues which comprises at least one intraoral device to be arranged in the oral cavity of the user; at least one set of cameras arranged in the intraoral device to capture at least one stereo image of the oral cavity of the at least one user; and at least one processing medium which receives the at least one stereo image; wherein at least the one processing medium comprises at least one trained neural network which analyzes the at least one stereo image to estimate at least one depth map; and wherein the at least one processing medium also comprises at least one block of location and mapping which sequentially integrates the at least one stereo image and the at least one depth map to the generated three-dimensional model.

18 Claims, 3 Drawing Sheets

(51) Int. Cl.
 *A61B 1/24* (2006.01)
 *G06T 7/593* (2017.01)
(52) U.S. Cl.
 CPC .... *G06T 7/593* (2017.01); *G06T 2207/10028* (2013.01); *G06T 2207/30036* (2013.01)
(58) Field of Classification Search
 USPC ........................................................ 345/419
 See application file for complete search history.

SYSTEM AND METHOD FOR CONSTRUCTING A THREE-DIMENSIONAL MODEL OF TEETH AND ADJOINING TISSUES IN AN ORAL CAVITY OF AT LEAST ONE USER

CROSS-REFERENCE DATA

This patent application is a continuation-in-part of a co-pending U.S. patent application Ser. No. 18/127,945 filed on Mar. 29, 2023 and entitled "SYSTEM AND METHOD FOR CONSTRUCTING A THREE DIMENSIONAL MODEL OF A DENTURE OF AT LEAST ONE USER," incorporated herein by reference in its entirety.

INTRODUCTION

The present invention refers to a system and method for building a three-dimensional model of teeth and adjoining tissues of at least one user intended for the field of dentistry.

The system and method of the invention make use of stereo techniques in conjunction with neural networks which allows the intraoral device to be used for image capture to only include the camera(s) necessary for the task and that all data processing is carried out outside the intraoral device, thus being considerably less complex and expensive than the state-of-the-art solutions.

In this sense, the system of the invention essentially comprises at least one intraoral device to be placed in the oral cavity of at least one user; at least one set of cameras arranged in the intraoral device to capture at least one stereo image of the oral cavity of the at least one user; and at least one processing medium which receives the at least one stereo image; wherein the at least one processing medium comprises at least one trained neural network which analyzes the at least one stereo image to estimate at least one depth map; and wherein the at least one processing medium further comprises at least one location and mapping block which sequentially integrates the at least one stereo image and the at least one depth map into the generated three-dimensional model.

On the other hand, the method of the invention essentially comprises the steps of: capturing at least one stereo image through at least one set of cameras arranged in at least one intraoral device; receiving at least one stereo image by at least one processing medium; analyzing the at least one stereo image to estimate at least one depth map through at least one trained neural network, comprised of the at least one processing medium; and sequentially integrating the at least one stereo image and the at least one depth map to the three-dimensional model generated through at least one location and mapping block comprised by the at least one processing medium.

Based on the system and method of the invention it is not only possible to improve the accessibility to this type of technology for dental patients thanks to the simplification of the physical device used in these procedures, but also a solution that attains greater accuracy than technologies using traditional modeling techniques is provided.

BACKGROUND

In the field of dentistry and its different specialties, the use of technologies that allow the modeling of patients' teeth is a widely spread practice due to the speed and simplicity of the process.

Most of these solutions contemplate the use of an intraoral device or scanner including at least one camera that uses any of the known principles for three-dimensional modeling, such as confocal microscopy, active stereo or structured light, in combination with an algorithm that typically performs the processing within the device itself In this sense, confocal microscopy is the most complex technique in terms of hardware to be used, being, therefore, more expensive to manufacture and implement. Such a technique estimates the depth of the image by varying the focus of a light source and filtering out-of-focus light with a lens. For each focus setting the camera receives light from the areas of the surface that are focused. Since the focus of the light is controlled and the geometry of the lens is known, there is a relationship that allows estimating the depth of the focused areas.

On the other hand, scanners using the active stereo technique capture pairs of images with a stereo camera, while projecting a pattern onto the surface. Then, an algorithm calculates the correspondences between both images using the projected pattern. The technique requires the arrangement of a pattern projector inside the scanner or intraoral device, also making its construction more complex.

Finally, scanners using the structured light technique project a known pattern of light onto the surface and capture images with a camera. Subsequently, by observing how the light pattern on the surface is deformed, an algorithm infers the topology and depth of such surface. Once again, scanners that use this type of technique must have additional hardware that makes them more expensive to manufacture.

In addition, as most of these solutions incorporate processing within the intraoral scanner, great caution must be taken with possible damage that may occur to the equipment, since a possible repair may entail high costs.

Therefore, there is a growing need not only for a system and method that allows simplifying the construction of the scanner or intraoral device through the use of a smaller number of components, as well as through the separation of the data acquisition and processing processes of the intraoral device but also improves the quality of three-dimensional modeling which has a substantial margin for improvement given the techniques used in the state of the art.

In the field of patents, there are solutions that point to devices or systems for the three-dimensional modeling of teeth in the dental field. For example, US Patent Application US20140146142AI describes a three-dimensional measurement device intended to measure in the absence of structured or active light projection including an image capture device and a data processor for images. The image capture device is capable of simultaneously or nearly simultaneously, capturing at least two images one of which is fully or partially included in the other. The included image describes a narrower field than the other and has greater accuracy than the other.

In this sense, document US20140146142AI, although it describes a device that has at least one camera that processes the information outside the device specifically in a computer adapted for it, the document does not make any reference to the use of neural networks previously trained with dental models during information processing, wherein only the use of several algorithms in the different stages of processing is mentioned. Since the processing in document US20140146142AI is carried out on the local computer at the office of the dentist who performs the procedure, the algorithms used cannot be highly complex since that would require a computer with a higher processing power. That would make that device within the reach of a few people.

Therefore, this document does not provide an algorithm that allows obtaining results superior to those existing in state of the art, since its processing capacity will be limited to the processing capacity of the user's computer, a situation that does not occur with the present invention, wherein by having a processing medium outside the intraoral device, which can be hosted in a cloud, it allows the processing capacity to increase considerably by being able to use, for example, neural networks trained with a high number of parameters which substantially improves the results of three-dimensional modeling.

Another example is the one disclosed in the International Patent Application WO2021250091AI which describes a method for the automatic segmentation of a dental arch that comprises acquiring a three-dimensional surface of the dental arch, in order to obtain a three-dimensional representation that comprises a vertex set generating virtual views from the three-dimensional representation, projecting the three-dimensional representation onto each two-dimensional virtual view to obtain an image that represents each vertex of the virtual view, processing each image using a deep learning network, performing an inverse projection of each image to assign to each vertex of the three-dimensional representation, one or more pixels of the images in which the vertex appears and to which it corresponds, and assigning one or more probability vectors to each vertex determining the class of dental tissues to which each vertex belongs.

When comparing the description of the document WO2021250091AI with the present application, it is possible to observe that although the document describes an intraoral device that uses trained neural network techniques for image processing, this algorithm is arranged within a processing module found in the intraoral device which considerably limits the processing capacity of the device, consequently limiting the complexity of the neural network used. This does not occur in the present invention, wherein all the processing is carried out outside the intraoral device thus not limiting the processing capacity and improving the quality of the three-dimensional modeling, allowing the reconstruction of the three-dimensional model to be obtained practically in real-time. In addition, the construction of the intraoral device is simplified as it only has the camera(s) necessary to obtain the images and the associated circuitry.

As can be seen from the documents described above the vast majority of these devices and systems do not have the objective of simplifying the intraoral device in its construction, with the consequent economic savings, but rather they address other types of problems such as avoiding the use of structured light, for example. Although there are solutions that perform data processing outside the intraoral device or that use neural networks for image analysis, these solutions are far from what is described by the present invention, wherein in addition to providing a simplified construction and use of the device, it allows processing to be carried out on a server located in a cloud. Together with not asking the user to buy expensive equipment with an on-site processing capacity, it allows for a notable improvement in the quality of three-dimensional modeling of the teeth and adjoining tissues, given that a much more complex processing algorithm can be used in combination with highly parameterized trained neural networks, to analyze the received images in order to determine the corresponding depth map.

Therefore, it is necessary to have a system and method not only to provide an intraoral device that is simpler and cheaper to build but also to improve the quality and speed of the three-dimensional modeling of the patient's teeth, so that the dentist in charge of the procedure can have the results in real-time. In addition, there is a need for a solution that allows avoiding the use of complex and high-cost equipment for data processing which the present invention makes possible through a server that receives the information obtained by the intraoral device directly from it or through a computer or other similar electronic device that works as a link and to view the results. This and other advantages associated with other aspects of the technology are described in greater detail below.

DESCRIPTION OF THE INVENTION

The invention refers to a system and method for building a three-dimensional model of teeth and adjoining tissues of at least one user in real time which simplifies the construction of an intraoral device to be used while improving the quality and speed of three-dimensional modeling.

According to a first preferred embodiment of the invention, the system for building a three-dimensional model of teeth and adjoining tissues of at least one user comprises:
- at least one intraoral device to be placed in the oral cavity of at least one user;
- at least one set of cameras arranged in at least one intraoral device to capture at least one stereo image of the oral cavity of the user; and
- at least one processing medium that receives at least one stereo image;
- wherein the at least one processing medium comprises at least one trained neural network that analyzes the at least one stereo image to estimate at least one depth map; and
- wherein the at least one processing medium further comprises at least one location and mapping block which sequentially integrates the at least one stereo image and the at least one depth map into the generated three-dimensional model.

In some embodiments, the system of the present invention works according to a passive stereo technique. This means that it uses pairs of synchronized images and an algorithm using trained neural networks that estimate the depths of the scanned surface without projecting anything onto it, as is the case in common state-of-the-art solutions. In other embodiments, the use of active stereo techniques with pattern projections is also contemplated and is included in the scope of the present invention.

In scenes with little texture and/or reflections, such as a patient's mouth, traditional passive stereo algorithms often perform weakly. Poor performance in these scenarios is caused by such traditional algorithms looking for key points in each image and then trying to match the key points in one image to those in the other (this is called stereo matching). With little texture and/or reflections key points are very ambiguous and algorithms make a lot of mistakes in processing.

The present invention uses an algorithm enriched through the use of a highly complex neural network instead of a traditional algorithm for stereo pairing. Such a neural network estimates the depth of images without using explicit key points and achieves significantly higher accuracy than traditional stereo-matching algorithms would. To achieve this accuracy, the neural network must be trained with highly realistic synthetic images and depths.

In this sense, the algorithm of the present invention, by understanding this neural network requires a high processing capacity. In order to avoid making the intraoral device more complex, which would make it more expensive, it is decided to carry out the processing outside the device either in external electronic equipment suitable for it or in a server arranged in a cloud. Based on the above, it is possible to solve both problems raised by the Application, such as simplifying the hardware used while improving the quality of the three-dimensional modeling of the patient's teeth which can be obtained in real-time by the user, thanks to the work of the neural network.

According to another embodiment of the invention, the processing medium further comprises at least one post-processing block which removes at least one noisy depth from the three-dimensional model, and recalculates the pose of the set of cameras. The post-processing is carried out using all the information captured during the scan carried out by the intraoral device. The recalculation of the pose of the set of cameras indicates that, as the images are being captured along with estimating the depth, the system of the invention estimates the position in which the set of cameras is. This is done to know how to combine the different depths. As the positions of the set of cameras are estimated, a cumulative error is also generated which must be corrected later in the post-processing block.

According to another embodiment of the invention, the system also comprises at least one receiving device that receives the stereo image from the set of cameras to send it to the processing medium.

According to another embodiment of the invention, the receiving device is at least one of a computer, a notebook, a tablet, and a smartphone.

According to another embodiment of the invention, the processing medium is arranged in the receiving device. This allows the users to carry out the data processing on their own equipment if they have one with the necessary processing capacity.

According to another embodiment of the invention, the receiving device comprises at least one display interface. The visualization interface allows the user to see the images acquired by the intraoral device and/or the three-dimensional modeling of the resulting teeth and adjoining tissues in real-time.

According to another embodiment of the invention, the processing medium is arranged in a cloud. This allows the user who does not have the necessary processing capacity to house the processing medium together with the neural network to have an option wherein the information collected by the intraoral device is sent directly to a server in the cloud or that occupies the receiving device as link port, which as mentioned above can correspond to a computer or a tablet, among others.

In addition, being the processing medium together with the neural network in a cloud, allows the system to simultaneously analyze the information coming from multiple intraoral devices sending back the respective three-dimensional modeling in real-time. Through this feature, it is possible to further reduce the cost of the system since it is not necessary to have a processing medium for each intraoral device in operation, as is the case with usual solutions.

According to another embodiment of the invention, the set of cameras comprises at least one first camera and at least one second camera. This allows obtaining the pairs of synchronized images necessary for the algorithm and the neural network to correctly estimate the depths of the scanned surface.

According to another embodiment of the invention, the intraoral device communicates with the processing medium wirelessly.

According to another embodiment of the invention, the intraoral device communicates with the processing medium via a communication cable.

According to another embodiment of the invention, the intraoral device communicates with the receiving device wirelessly.

According to another embodiment of the invention, the intraoral device communicates with the receiving device via a communication cable.

According to another embodiment of the invention, the receiving device communicates with the cloud wirelessly.

According to another embodiment of the invention, the intraoral device further comprises at least one battery which allows the intraoral device to function without the need to be directly connected to a power source, such as a plug.

On the other hand, according to a second preferred embodiment of the invention, a method is also described for constructing a three-dimensional model of teeth and adjoining tissues of at least one user, which comprises the steps of:
 capturing at least one stereo image through at least one set of cameras arranged in at least one intraoral device;
 receiving the at least one stereo image by at least one processing medium;
 analyzing the stereo image to estimate at least one depth map through at least one trained neural network comprised of at least one processing medium; and
 sequentially integrating the stereo image and at least one depth map to the three-dimensional model generated through at least one location and mapping block comprised of the processing medium.

As mentioned above, when capturing images, the intraoral device begins to send stereo images in real-time to a link equipment, such as a computer, which then sends the information to a cloud server wherein the processing medium is located, or directly sends the images to the processing medium arranged in the computer. Once the images are available to be analyzed by the processing medium the neural network specifically trained for this task analyzes each stereo image sent and estimates a depth map from them.

The depth map together with the stereo image, are integrated into the reconstruction generated up to that moment through at least one location and mapping block which compares the information it receives with the partial reconstruction of the scene and predicts a pose for the stereo image.

According to another embodiment of the invention, the method further comprises removing at least one noisy depth from the three-dimensional model and recalculating the pose of the set of cameras through at least one post-processing block comprised of the processing medium.

According to another embodiment of the invention, the method further comprises, before step c), receiving the stereo image from the set of cameras by at least one receiving device to subsequently send it to the processing medium.

According to another embodiment of the invention, the method further comprises displaying the information sent and received from the processing medium through at least one display interface arranged on the receiving device.

According to another embodiment of the invention, the method further comprises generating the three-dimensional model of the teeth of the user in real-time and sending it to the display interface.

Finally, according to a third preferred embodiment of the invention, a computer-readable storage medium is also described, comprising instructions that when executed by at least one processor, cause the processor to perform the method for constructing a three-dimensional model of adjoining tissues of at least one user.

The above discussion illustrates an important difference between the present invention and the prior solutions known in the art. Some embodiments of the present system use a powerful novel neural model that allows it to estimate depths using exclusively the passive stereo technique. This means that the sensors of the intraoral device are considerably less complex and less expensive since they consist only of at least one ordinary camera and a circuit to synchronize them.

In addition, both the count of the depths from the stereo images and the reconstruction process and post-processing can be executed on a server arranged in the cloud, wherein the processing medium is located together with the trained neural network. In this case, the dentist's computer only sends the information obtained by the intraoral device to this data cloud and allows the status of the reconstruction to be viewed in a real-time display interface, so that the dentist can control the process. In contrast, traditional scanners perform reconstruction and post-processing on the dentist's own computer, which requires the computer to have hardware powerful enough to accommodate the used processing algorithms, wherein often the algorithm used by these solutions must be adapted to this type of computers, going directly to the detriment of the quality of the obtained three-dimensional modeling which does not occur in the present invention, wherein the quality of the modeling is improved as this limitation does not exist in terms of the processing capacity.

Finally, none of the state-of-the-art solutions provides the possibility of using a single processing medium to analyze the data sent by multiple intraoral devices which optimizes the use of resources and reduces the costs associated with the implementation of the system, allowing greater accessibility to this type of technology by dentists and patients.

BRIEF DESCRIPTION OF THE FIGURES

As part of the present invention, the following representative figure thereof is exhibited which shows a preferred configuration of the invention and, therefore, should not be considered as limiting the definition of the claimed subject matter.

DETAILED DESCRIPTION OF THE FIGURES

Figure 1:
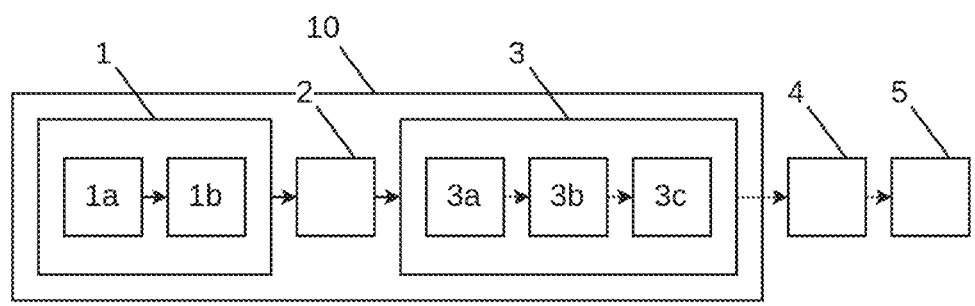
FIG. 1 shows a block diagram of the intraoral scanning process according to the state of the art.

With reference to the accompanying Figures, FIG. 1 shows a block diagram of the traditional intraoral scanning process to obtain a three-dimensional representation of a patient's teeth. Specifically, a first stage of data capture and reconstruction (1) is observed which is made up of two sub-stages. The first sub-stage (Ia) points to the actual scanning carried out by a specialist such as a dentist, in the patient's mouth. This is done through a physical device that is inserted into the user's mouth which includes at least one data capture device. During the scanning, the scanner sends the data it captures to the dentist's computer in real-time, wherein these technique scanners generally work under the theoretical principles of confocal microscopy or structured light (active stereo), which are usually images, depths, and measurements of an Inertial Measurement Unit (IMU) comprising an accelerometer and gyroscope to measure angular velocities and accelerations. Once the information obtained by the scanner is sent to the specialist's computer, it sequentially integrates the images, depths, and other measurements to estimate the pose of the camera in each image and thus build the 3D model (sub-stage (1b)). In this way, a first 3D model of the patient's teeth is obtained which is still inaccurate and dirty (block (2)).

Because the 3D model obtained in this first stage is not optimal for use in dental treatments, a post-processing stage (3) is required, wherein this first 3D model is cleaned through the removal of noisy points or points that do not correspond to the adjoining tissues (sub-stage (3a)). After that, the dentist's computer recalculates the reconstruction using all the information received during the scanning (sub-stage (3b)). Finally, the poses and depths are optimized to minimize the reprojection error (sub-stage (3c)), which corresponds to the difference between the captured images and the images generated from the 3D model reconstruction, after which a corrected and clean 3D model is obtained (block (4)) which does allow its use by the specialist to develop a specific treatment for the patient (block (5)), among which we can mention invisible aligners, relaxation bite planes, dental crowns, among others.

It should be noted that these state-of-the-art techniques require the specialist to have a computer (10) with high resources in terms of its processing capacity, given the number of images to be processed and to be able to execute the processing algorithms necessary to generate the 3D model, wherein at least the stages described by blocks (1), (2) and (3) must be carried out.

Figure 2:
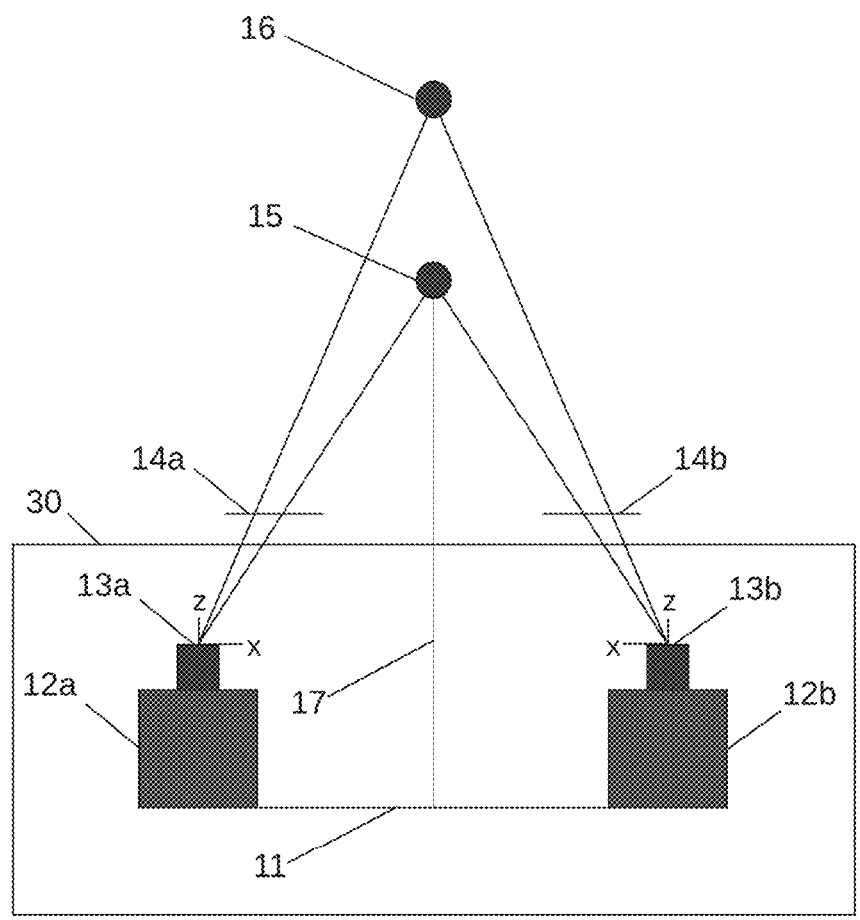
FIG. 2 shows a general scheme of the passive stereo technique according to a preferred configuration of the invention.

On the other hand, FIG. 2 shows a general scheme of the passive stereo technique used by the present invention, wherein it is possible to understand how the scanner or intraoral device (30) of the technology operates. In this sense, in the embodiment exhibited in FIG. 2, the intraoral device (30) comprises two left and right chambers (12a, 12b) positioned on a baseline (11), wherein the chambers (12a, 12b) in turn comprise a left and right lens (13a, 13b), respectively. The left and right cameras (12a, 12b) may be positioned parallel to the baseline (11) or at an angle to it.

Each camera (12a, 12b) of the intraoral device (30) forms an image plane (14a, 14b) through which the real points (15, 16) are displayed in each image obtained by the cameras (12a, 12b). As previously mentioned, the intraoral device (30) uses the passive stereo technique to estimate the depth (17) of the scanned surface which is achieved through pairs of synchronized images and an algorithm that processes the images without the need to project anything on the images, as occurs in other state-of-the-art solutions to address this problem.

This is extremely relevant in scenes with little texture and/or reflections, such as a patient's mouth wherein traditional passive stereo algorithms tend to work weakly because the traditional algorithms search for key points in each image and then try to relate these key points of one image to those of the other (stereo matching). Since the inside of the mouth has surfaces that mostly have little texture and/or reflections, the key points are very ambiguous and difficult to locate so these traditional algorithms make a lot of mistakes, giving inaccurate results.

The present invention, by using a neural network instead of a traditional algorithm for stereo matching, does not need to locate explicit key points for the calculation of the image's depth which improves the accuracy in situations of low texture and/or or reflections such as inside the mouth of patients. To achieve that accuracy, the neural network must be trained with highly realistic synthetic images and depths. Synthetic images can also be modeled in rendering software, in which they can be displayed with regular illumination or with a projected pattern, so that the neural network can be trained to infer depth properly upon any method.

Figure 3:
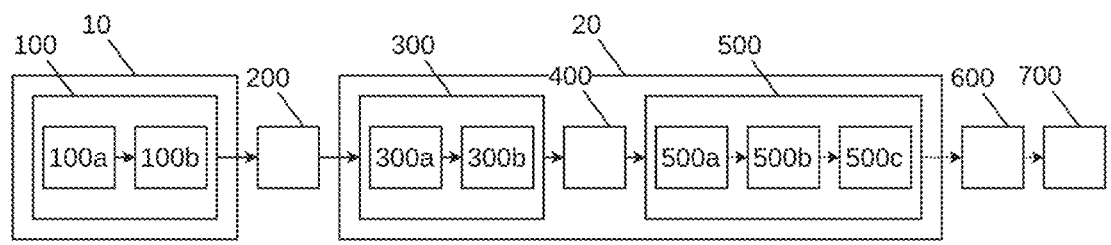
FIG. 3 shows a block diagram of the intraoral scanning process according to a preferred configuration of the present invention.

Finally, FIG. 3 shows a block diagram of the intraoral scanning process according to a preferred embodiment of the invention. Specifically, a first data capture stage (100) is shown, which is divided into two sub-stages. The first aims at the capture of pairs of synchronized images (stereo images) by the specialist through the scanner or intraoral device, to later transmit them to his computer, wirelessly or through a data cable (sub-stage (I00a)). Then the computer transmits the stereo images in real-time to a server or cloud (sub-step (100b)). The intraoral device preferably consists of two cameras and a circuit that synchronizes the capture of both cameras, wherein the depths are calculated by a neural network from these images which preferably resides in the same cloud where the images are received from the intraoral device. As a result of this first stage of data capture (100), a stereo image stream (block (200)) is obtained from the intraoral device to the specialist's computer and then to the cloud.

This is an important difference between what is described by the state of the art and the present invention, since as it can be seen, the system of the invention only requires using the specialist's computer (10) in this data capture stage (100), after which the information is processed in the cloud wherein the processing algorithms are housed together with the neural network. This prevents the specialist from having a computer with high processing power wherein he could even only have an electronic device that is capable of connecting to the cloud, such as a tablet or a smartphone.

After this first stage of data capture and sending information to the cloud (100) in which the flow of stereo images (200) is obtained, a reconstruction stage follows in the cloud (300) which comprises a depth map calculation sub-stage (300a) for each pair of images based on the use of a neural network, and a sequential integration sub-stage to the 3D reconstruction of the depth maps and the images (300b). The neural network compares the two images (RGB, for example) and estimates the depth of each pixel based on the relative movement of the objects between both images. In contrast, traditional scanners estimate depth using a confocal microscope or structured light which are less accurate, requiring surfaces with appreciable texture. As a result of this reconstruction stage in the cloud (300), an inaccurate and dirty 3D model is obtained (block (400)).

Once the first 3D model (400) is obtained, a post-processing stage must be carried out in the cloud (500) which comprises three sub-stages. The first aims at cleaning the 3D reconstruction (500a) by removing noisy points or points that do not correspond to the adjoining tissues, after which the processing medium recalculates the reconstruction (500b) using all the information received during the scanning and data capture stage (100). Finally, the poses and depths (500c) are optimized to minimize the reprojection error, which as mentioned above, corresponds to the difference between the captured images and the images generated from the reconstruction.

As a product of these two reconstruction and post-processing stages in the cloud, a corrected and clean 3D model is obtained (block (600)) with improved accuracy as compared to the state of the art, wherein the specialist can download the 3D model generated in the cloud to perform a dental treatment (700), such as invisible aligners, relaxation bite planes, dental crowns, among others.

In this sense, it is important to highlight the importance of the fact that the reconstruction (300) and post-processing (500) stages are carried out in a cloud (20) wherein the processing medium is located, comprising the trained neural network and the algorithms that make up the location and mapping block which sequentially integrates the at least one stereo image and the at least one depth map into the generated three-dimensional model. This not only prevents the specialist from having a device that includes a high processing power, as mentioned above, but also allows having processing tools in the cloud with a higher capacity than those used in the state of the art which are limited, either by the processing capacity of the intraoral device or the specialist's computer. This results in a solution wherein the specialist receives the results with the corrected and clean 3D model in real-time, thanks to the high processing power and the neural network that allows obtaining more accurate results in less time.

Finally, the possibility of the system of the invention to operate with multiple intraoral devices through a single cloud is also highlighted which allows to reduce the costs associated with the implementation of the system significantly, making it accessible to the majority of specialists for which only one processing medium is needed, which is not the case in the state-of-the-art solutions, whereby the entire processing system must be paid for each time a specialist purchases the product.

NUMERICAL REFERENCES

1 Data capture and reconstruction
1a Scanning by the specialist and sending data to the computer
1b Reconstruction of the 3D model
2 Inaccurate and dirty 3D model
3 Post-processing
3a Cleaning up the inaccurate and dirty 3D Model
3b Recalculate the reconstruction
3c Optimization of poses and depths
4 Corrected and clean 3D model
5 Treatment
I0 Specialist computer
11 Baseline
12a Left chamber
12b Right chamber
13a Left lens
13b Right lens
14a Left image plane
14b Right image plane
15, 16 Real point
17 Depth
20 Cloud
30 Intraoral device
I00 Data Capture
I00a Scanning by the specialist and sending data to the computer
100b Real time stereo image transmission to cloud
200 Stereo image stream
300 Cloud reconstruction
300a Depth map calculation
300b Sequential Integration to 3D Reconstruction
400 Inaccurate and dirty 3D Model
500 Post-processing in the cloud 500a Clean up of inaccurate and dirty 3D Model
500b Recalculate Reconstruction
500c Optimization of poses and depths
600 Corrected and clean 3D model
700 Treatment

What is claimed is:

1. A system to build a three-dimensional model of an at least one user's teeth and adjoining tissues, the system comprising:
   at least one intraoral device configured to be arranged in the oral cavity of at least one user;
   at least one set of cameras arranged in the at least one intraoral device at known positions thereon and configured to capture at least one stereo image comprising at least a pair of synchronized images of the same area of the oral cavity of the at least one user; and
   at least one processing medium which receives the at least one stereo image, and comprising at least one trained neural network;
   wherein the at least one processing medium is arranged for:
      receiving the at least one pair of synchronized images;
      estimating, using the at least one pair of synchronized images, a depth map using the trained neural network, by estimating a depth of each pixel in the pair of images and using the relative position of objects that appear in both images;
      generating, using at least one location and mapping block, a three-dimensional model by sequentially integrating the at least one pair of images and the depth map together;
      removing, from the three-dimensional model, projected points in the model that are unrelated to adjoining tissues;
      regenerating the three-dimensional model after the points are removed; and
      optimizing, in the regenerated three-dimensional model, poses and depths of adjoining tissues to minimize a reprojection error between the at least one pair of synchronized images and the projected points in the three-dimensional model, thereby producing a corrected three-dimensional teeth and adjoining tissues model.

2. The system according to claim 1, wherein the at least one processing medium also comprises at least one post-processing block which eliminates at least one noisy depth of the three-dimensional model and that recalculates the pose of at least one set of cameras.

3. The system according to claim 1, further comprising at least one receiving device which receives at least one stereo image from at least one set of cameras, to send it to at least one processing medium.

4. The system according to claim 3, wherein the at least one receiving device is at least one of a computer, a notebook, a tablet and a smartphone.

5. The system according to claim 3, wherein the at least one receiving device comprises at least one display interface.

6. The system according to claim 1, wherein the at least one set of cameras comprises at least a first camera and at least a second camera.

7. The system according to claim 1, wherein the at least one intraoral device communicates wirelessly with at least one processing medium.

8. The system according to claim 1, wherein the at least one intraoral device communicates through a communication cable with at least one processing medium.

9. The system according to claim 3, wherein the at least one intraoral device communicates wirelessly with at least one receiving device.

10. The system according to claim 3, wherein the at least one intraoral device communicates through a communication cable with at least one receiving device.

11. The system according to claim 3, wherein the at least one receiving device communicates wirelessly with at least one cloud.

12. The system according to claim 1, wherein the at least one intraoral device also includes at least one battery.

13. A method to build a three-dimensional model of teeth and adjoining tissues of at least one user, comprising:
   a) capturing at least one stereo image comprising at least a pair of synchronized images through at least one set of cameras arranged in at least one intraoral device at known positions to each other;
   b) receiving the at least one stereo image at the at least one processing medium comprising at least one trained neural network;
   c) estimating by the at least one processing medium, using at least one pair of synchronized images, a depth map using the trained neural network, by estimating a depth of each pixel in the pair of images and using the relative position of objects that appear in both images;
   d) generating by the at least one processing medium, using at least one location and mapping block, a three-dimensional model by sequentially integrating at least one pair of images and the depth map together;
   e) removing, from the three-dimensional model, projected points in the model that are unrelated to adjoining tissues;
   f) regenerating the three-dimensional model after the points are removed; and
   g) optimizing, in the regenerated three-dimensional model, poses and depths of adjoining tissues to minimize a reprojection error between at least one pair of synchronized images and the projected points in the three-dimensional model,
   thereby producing a corrected three-dimensional teeth and adjoining tissues model.

14. The method according to claim 13, further comprising eliminating at least one noisy depth of the three-dimensional model and recalculating the pose of at least one set of cameras through at least one post-processing block.

15. The method according to claim 13, wherein the method further comprises before stage c), receiving at least one stereo image from at least one set of cameras by at least one receiving device to subsequently send it to at least one processing medium.

16. The method according to claim 15, wherein the method further comprises visualizing the information sent and received from at least one processing medium through at least one display interface arranged in at least one receiving device.

17. The method according to claim 16, wherein the method further comprises generating the three-dimensional model of teeth and adjoining tissues of at least one user in real-time and sending it to at least one display interface.

18. A computer-readable storage medium, containing instructions that, when they are executed by at least one processor, make at least one processor perform the method of claim 13.

* * * * *